United States Patent
Mistrik et al.

(10) Patent No.: US 12,303,531 B2
(45) Date of Patent: May 20, 2025

(54) MOLECULAR COMPLEX ASSEMBLY PARTICLES COMPRISING BIS-R1,R2-DITHIOCARBAMATE-METAL COMPLEX AND A LIGAND, METHOD OF PREPARATION AND USE THEREOF

(71) Applicant: PALACKY UNIVERSITY OLOMOUC, Olomouc (CZ)

(72) Inventors: Martin Mistrik, Olomouc (CZ); Jiri Bartek, Greve (DK); Zdenek Skrott, Ruzdka (CZ); Petr Dzubak, Brodek u Prerova (CZ); Marian Hajduch, Moravsky Beroun (CZ)

(73) Assignee: PALACKY UNIVERSITY OLOMOUC, Olomouc (CZ)

( * ) Notice: Subject to any disclaimer, the term of this patent is extended or adjusted under 35 U.S.C. 154(b) by 274 days.

(21) Appl. No.: 17/282,142

(22) PCT Filed: Oct. 8, 2019

(86) PCT No.: PCT/EP2019/077222
§ 371 (c)(1),
(2) Date: Apr. 1, 2021

(87) PCT Pub. No.: WO2020/074514
PCT Pub. Date: Apr. 16, 2020

(65) Prior Publication Data
US 2022/0000914 A1    Jan. 6, 2022

(30) Foreign Application Priority Data
Oct. 8, 2018 (EP) .................................... 18199181

(51) Int. Cl.
  A61K 33/34     (2006.01)
  A61K 9/16      (2006.01)
  A61K 47/34     (2017.01)

(52) U.S. Cl.
  CPC ............ *A61K 33/34* (2013.01); *A61K 9/1635* (2013.01)

(58) Field of Classification Search
  None
  See application file for complete search history.

(56) References Cited

U.S. PATENT DOCUMENTS 6,548,540 B2 *  4/2003  Kennedy ................ A61K 33/34
                                                  514/483
11,045,553 B2 *  6/2021  Li ...................... A61K 47/6929
                    (Continued)

OTHER PUBLICATIONS

Raynoso-Garcia et al. Stabilization of Silver Nanoparticles with a Dithiocarbamate Ligand and Formation of Nanocomposites by Combination with Polythiophene Derivative Nanoparticles. Advances in Condensed. Advances in Condensed Matter Physics, vol. 2018, 9 pages. Article ID 4376051. Aug. 1, 2018. (Year: 2018).*

(Continued)

*Primary Examiner* — Lakshmi S Channavajjala
(74) *Attorney, Agent, or Firm* — Notaro, Michalos & Zaccaria P.C.

(57) ABSTRACT

A complex particle form of dithiocarbamate-metal compound and at least one ligand, that is a polymer or a detergent is disclosed. The complex particle form is obtained by a process having a sequential or simultaneous addition of individual components, resulting in their self-assembling. The dry form or aqueous dispersion of the complex particle form is suitable for medicinal per-oral, topical and parenteral administration and for therapy and imaging of cancer.

13 Claims, 7 Drawing Sheets

(56) References Cited

U.S. PATENT DOCUMENTS

| | | | |
|---|---|---|---|
| 2003/0229064 A1 | 12/2003 | Kennedy | |
| 2005/0096304 A1 | 5/2005 | White et al. | |
| 2012/0301528 A1* | 11/2012 | Uhlmann | A61Q 17/005 977/773 |
| 2017/0095504 A1* | 4/2017 | Sarangapani | A61K 31/715 |

OTHER PUBLICATIONS

Naharros-Molinero et al. Direct and Reverse pliuronic micelles: design and characterization of promising drug delivery nanosystems. Pharamceutics, 14: 2628, pp. 1-25. (Year: 2022).*

Mathew et al. N, N'-Methylene-bis-acrylamide-Crosslinked Polyacrylamides as Supports for Dithiocarbamate Ligands for Metal Ion Complexation. Polymer International, 28:201-208. (Year: 1992).*

N, N'-Methylenebis(acrylamide) Sigma Aldrich. 2023 Millipore Sigma. 9 pages (Year: 2023).*

Li et al. stable water-soluble quantum dots capped by poly(ethylene glycol) modified dithiocarbamate. (Colloidal and Surfaces A: Physicochemical and Engineering Aspects: 410:144-152). (Year: 2012).*

Venkatesh K. Rudrapatna et al: "Abstract 5526: Development of dithiocarbamate/ metal complexes in Pluronic micelles for the treatment of malignancies", Cancer Research, vol. 70, No. 8 supplement, Apr. 1, 2010 (Apr. 1, 2010), XP055578684, DOI: 10.1158/1538-7445.AM10-5526, retrieved Mar. 31, 2021.

You Chunwan et al: "Antitumor activity of PEG-PCUdithiocarbamate-copper nanoparticles", Nanomedicine: Nanotechnology, Biology and Medicine, vol. 12, No. 2, Mar. 9, 2016 (Mar. 9, 2016), p. 472, XP029459218, ISSN: 1549-9634, DOI: 10.1016/J.NANO.2015.12.078, retrieved Mar. 31, 2021.

Tomasello Marianna F et al: New comprehensive studies of a gold(III) Dithlocarbamate complex with proven anticancer properties: Aqueous dissolution with cyclodextrins, pharmacokinetics and upstream inhibition of the ubiquitin-proteasome pathway•, European Journal of Medicinal Chemistry, Editions Scientifique Elsevier, Paris, FR, vol. 138, Jun. 19, 2017 (Jun. 19, 2017), pp. 115-127, XP085163728, ISSN: 0223-5234, DOI: 10.1016/J.EJMECH.2017.06.013, retrieved Mar. 31, 2021.

Rumei Cheng et al: "Equilibrium and Molecular Mechanism of Anionic Dyes Adsorption onto Copper(II) Complex of Dithiocarbamate-Modified Starch", Langmuir, vol. 26, No. 2, Jan. 19, 2010 (Jan. 19, 2010), pp. 752-758, XP055578628, US ISSN: 0743-7463, DOI: 10.1021/la9039489 , retrieved Mar. 31, 2021.

Skrott Z, et al., "Alcohol-abuse drug disulfiram targets cancer via p97 segregase adaptor NPL4." Nature., Dec. 14, 2017; 552 (7684):194-199. doi: 10.1038/nature25016. Epub Dec. 6, 2017. PMID: 29211715; PMCID: PMC5730499, retrieved Mar. 31, 2021.

International Search Report and Written Opinion for corresponding PCT application No. PCT/EP2019/077222, mailed Dec. 18, 2019.

* cited by examiner

Figure 1.

| DLS Multiple narrow modes | Size (d.nm.) |
|---|---|
| PVP-40 according example 1 | 52,9 ± 7,7 |
| PVP-40 according example 2 | 46,4 ± 1,9 |
| Hyaluronic acid | 1076,27 ± 62,94 |
| Sodium deoxycholate | 46,4 ± 1,9 |
| Soluplus® | 53,4 ± 2,7 |
| Solutol HS 15 5% | 45,08 ± 23,32 |
| Methylcelulose 0,2% | 233,6 ± 98,13 |
| Gelofusine 4% | 28,1 ± 10,2 |
| Cremophor 5% | 262,4 ± 4,87 |
| HPMA 5% | 69,54 ± 11,99 |
| Captisol 5% | 155,93 ± 13,93 |
| PVP 360 5% | 451,13 ± 342,62 |
| Chondroitin sulphate 5% | 298,17 ± 32,07 |
| Ficol 400 5% | 11,46 ± 3,68 |
| Kollidon 17 5% | 56,6 ± 12,16 |
| HES 5% | 57,25 ± 20,93 |
| Kolliphor EL 5% | 158,67 ± 24,31 |
| Pluronic F-127 5% | 74,54 ± 9,5 |
| Lutrol 5% | 45,44 ± 3,51 |
| Hydroxypropylmethyl cellulose 1% | 330 ± 23,16 |

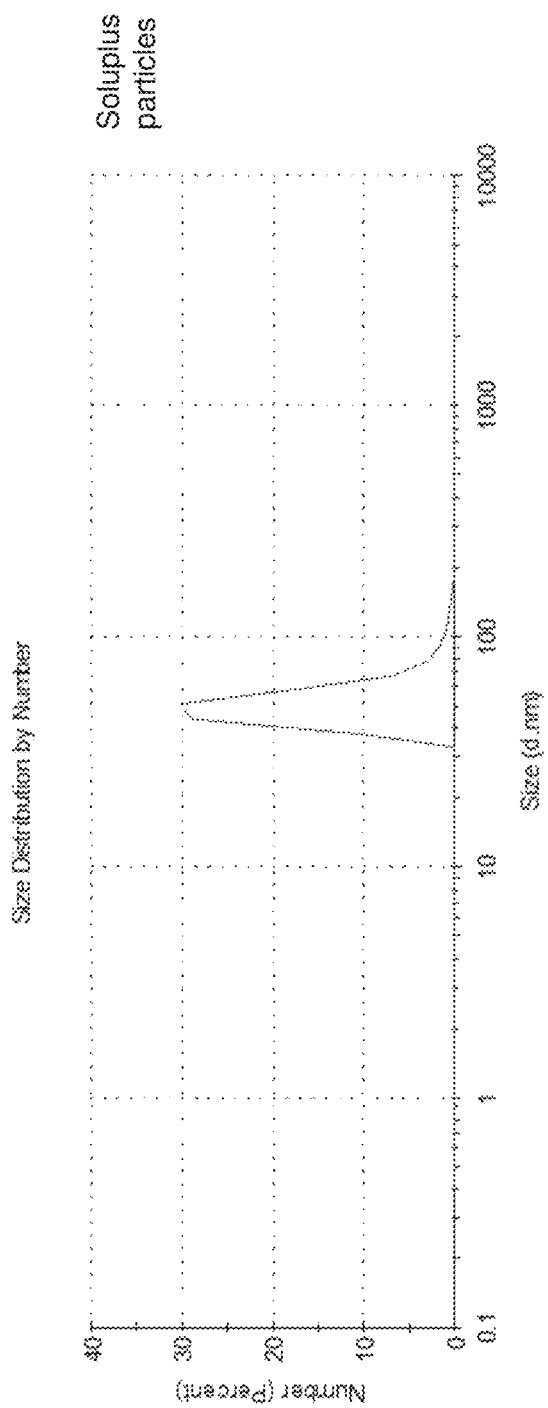
Figure 2. - continued

Figure 4.

| Complex particle of dithiocarbamate copper compound with following excipients | IC50 (µM) for tested cell lines | | | | | | | | | |
|---|---|---|---|---|---|---|---|---|---|---|
| | CCRF-CEM | CEM-DNR | K562 | K562-TAX | HCT116 | HCT116p53-/- | A549 | U2OS | BJ | MRC5 |
| Hyaluronic acid | - | 0,111 | 0,053 | 0,107 | 0,028 | 0,042 | 0,334 | 0,121 | 0,87 | 0,087 |
| Chondroitin sulphate | 0,015 | 0,059 | 0,104 | 0,06 | 0,056 | 0,046 | 0,072 | 0,043 | 0,657 | 0,118 |
| Methylcellulose | - | 0,128 | 0,107 | 0,156 | 0,134 | 0,115 | 0,104 | 0,363 | 0,115 | 0,124 |
| HES (Voluven®) | - | 0,049 | 0,049 | 0,091 | 0,049 | 0,049 | 0,049 | 0,049 | 0,116 | 0,116 |
| Pluronic® F-127 | 0,0084 | 0,034 | 0,042 | 0,037 | 0,036 | 0,026 | 0,046 | 0,033 | 0,18 | 0,038 |
| PVP 40 | 0,027 | 0,153 | 0,085 | 0,138 | 0,134 | 0,119 | 0,15 | 0,181 | 0,376 | 0,11 |
| PVP 360 | - | 0,124 | 0,053 | 0,113 | - | 0,103 | 0,13 | 0,204 | 0,273 | 0,109 |
| Cremophor | 0,107 | 0,134 | 0,1 | 0,145 | 0,174 | 0,475 | 0,164 | 0,665 | 0,584 | 0,699 |
| Soluplus® | 0,014 | 0,157 | 2,18 | 0,073 | 0,128 | 0,128 | 0,108 | 0,192 | 2,674 | 0,434 |
| Solutol HS® 15 | 0,011 | 0,042 | 0,043 | 0,043 | 0,04 | 0,035 | 0,042 | 0,038 | 0,135 | 0,047 |
| Succinylated gelatine (Gelaspan®) | - | 0,111 | 0,075 | 0,114 | 0,118 | 0,118 | 0,498 | 0,066 | 0,118 | 0,118 |
| Dithiocarbamate copper compound in DMSO | 0,0065 | 0,158 | 0,021 | 0,076 | 0,284 | 0,094 | 0,181 | 0,093 | 0,527 | 0,175 |

Figure 5.

| Complex particle of dithiocarbamate copper compound with following excipients | Change in spheroids area after 3 days of treatment (% of untreated controls) | | | | | | | | | | | |
|---|---|---|---|---|---|---|---|---|---|---|---|---|
| | Test concentration 10 µM | | | | Test concentration 1 µM | | | | Test concentration 0.1 µM | | | |
| | HCT116 | DLD-1 | DU145 | HeLA | HCT116 | DLD-1 | DU145 | HeLA | HCT116 | DLD-1 | DU145 | HeLA |
| Hyaluronic acid | 0 | 73 | 0 | 0 | 15 | 69 | 0 | 0 | 54 | 75 | 77 | 66 |
| Chondroitin sulphate | 0 | 0 | 0 | 0 | 40 | 63 | 82 | 53 | 87 | 105 | 91 | 109 |
| Methylcellulose | 0 | 40 | 0 | 0 | 0 | 60 | 0 | 0 | 48 | 69 | 83 | 45 |
| HES (Voluven®) | 0 | 0 | 0 | 0 | 52 | 72 | 70 | 64 | 52 | 95 | 83 | 79 |
| Pluronic® F-127 | 0 | 0 | 0 | 0 | 0 | 0 | 0 | 0 | 53 | 69 | 72 | 67 |
| PVP 40 according to example 1 | 0 | 0 | 0 | 0 | 0 | 60 | 60 | 25 | 58 | 91 | 85 | 65 |
| PVP 40 according to example 2 | 0 | 0 | 0 | 0 | 0 | 62 | 65 | 30 | 57 | 80 | 84 | 75 |
| PVP 360 | 0 | 51 | 0 | 0 | 15 | 64 | 68 | 56 | 77 | 89 | 91 | 96 |
| Cremophor | 32 | 58 | 50 | 36 | 48 | 73 | 78 | 71 | 58 | 90 | 95 | 81 |
| Soluplus® | 0 | 12 | 0 | 0 | 31 | 62 | 54 | 0 | 63 | 63 | 92 | 58 |
| Solutol® HS 15 | 0 | 0 | 0 | 0 | 76 | 81 | 54 | 0 | 95 | 103 | 100 | 106 |
| succinylated gelatine (Gelaspan®) | 72 | 83 | 74 | 53 | 56 | 84 | 84 | 87 | 76 | 95 | 90 | 94 |
| Salmon sperm DNA | 18 | 0 | 0 | - | 80 | 50 | 77 | - | 81 | 80 | 95 | - |
| Kollidon®17 | 0 | - | - | - | 50 | - | - | - | 98 | - | - | - |
| Ficol 400 | 81 | - | - | - | 98 | - | - | - | 101 | - | - | - |
| Kolliphor® EL | 82 | - | - | - | 96 | - | - | - | 100 | - | - | - |
| Captisol® | 0 | - | - | - | 87 | - | - | - | 102 | - | - | - |
| Sodium deoxycholate | 89 | - | - | - | 88 | - | - | - | 89 | - | - | - |
| Dithiocarbamate copper compound in DMSO | 103 | 84 | 0 | 0 | 104 | 88 | 95 | 103 | 102 | 89 | 97 | 103 |

MOLECULAR COMPLEX ASSEMBLY PARTICLES COMPRISING BIS-R1,R2-DITHIOCARBAMATE-METAL COMPLEX AND A LIGAND, METHOD OF PREPARATION AND USE THEREOF

FIELD OF THE INVENTION

The present invention relates to particles comprising mononuclear or multinuclear molecular complex particles (or molecular complex assembly particles) comprising at least one bis-R1,R2-dithiocarbamate-metal complex and at least one ligand. The ligand is typically a water-soluble pharmaceutically acceptable excipient substance: a polymer or a detergent. The particles are useful for medical applications, including cancer treatment and diagnostics. A process for producing such particles is disclosed.

BACKGROUND ART

R1,R2-dithiocarbamates (DTC) are strong metal ion chelators known in the literature. Once DTC reacts with metal form new chemical entity—compound (dithiocarbamate metal chelate). Some of these compounds display anticancer activity in cellular systems employing various cancer cell models. However, the compounds with proposed antitumor activity are not water soluble, which makes it particularly difficult to administer such complex to patients; also the compounds show low preferential toxicity towards cancer cells and thus nearly narrow therapeutic index. Both limitations can be overcome by the present invention.

Dithiocarbamates (DTC), particularly in chelate complex with various bivalent metals, exhibit promising anticancer activity in various preclinical models. Metal chelating properties of DTC's are known for a long time, as well as their antitumor activity. Several patent documents have covered the use of dithiocarbamate complexes with heavy metals, especially with copper, zinc, gold or silver, as a treatment strategy for various malignancies (see e.g. US20030229064, US20050096304). However, none of these patent documents has been translated to practical use in humans so far. Apparently, the main obstacle for the use of dithiocarbamate-metal compounds in the clinical routine are unfavourable pharmacologic properties, namely stability and water-based formulation capabilities. For instance, for the most promising anticancer compound which is bis(diethyldithiocarbamate)copper(II) (or copper bis(diethyldithiocarbamate)), the solubility constant in water is only in the range of nanograms per litre, which is insufficient to deliver therapeutic doses in patients.

Formulation of bis-R1,R2-dithiocarbamate metal complexes in albumin solution was mentioned in Skrott Z. et al.: Nature, (2017) 552(7684). However, the use of proteins in the formulation involves several disadvantages, technical as well as hygienic, toxicology and ethical issues. Immunoreactivity issues may occur, and during testing in animal models, different types of proteins need to be used. The stability of formulations comprising proteins may be rather low, and the formulations are prone to denaturation due to low or high pH values or due to higher temperatures, or prone to decomposition by action of proteases. Only few proteins are authorized for pharmaceutical use. Furthermore, only few proteins are commercially available on a large scale, and they are rather costly due to the costly production and/or purification.

The present invention thus aims at providing bioavailable particles comprising bis-R1,R2-dithiocarbamate metal complex, which would be stable, economical, versatile, and would not involve ethical, hygienic, toxicology and immunoreactivity issues.

SUMMARY OF THE INVENTION

Object of the present invention is a particulate form of dithiocarbamate-metal complexes with ligands in the form of molecular complex assembly particles. The ligands are typically water-soluble polymers and/or detergents such as cholate derivatives.

The term "water-soluble" refers to substances having the water-solubility (i.e., saturated aqueous solution concentration) of at least 0.001% w/w (i.e., 0.01% w/w), preferably at least 0.01% w/w or at least 0.1% w/w or at least 1% w/w, in deionized water.

Water-soluble polymers are substances containing monomeric units, typically repeating monomeric units, and having water solubility of at least 0.001% w/w, preferably at least 0.01% w/w or at least 0.1% w/w, in deionized water.

Water-soluble detergents are surface active agents having water solubility of at least 0.001% w/w, preferably at least 0.01% w/w or at least 0.1% w/w, in deionized water.

Preferred polymers and/or detergents are those that are acceptable for use as pharmaceutical excipients. Such ligands have a low or no toxicity and are tested and registered for use in pharmaceutical formulations, such as therapeutical or diagnostic preparations.

The particles of the present invention are suitable for use as anticancer drugs or as diagnostic agents. The particle of the present invention comprises or consists of dithiocarbamate-metal complex and at least one ligand, and the particle is in the form of a molecular complex assembly typically involving multiple molecules of dithiocarbamate-metal complex and multiple ligand molecules of one or several types. The particle preferably has the size in the range of 1-2000 nm. The particulate form is preferably substantially free of organic solvents.

Preferably, the complex particle comprises or consists of dithiocarbamate-copper complex and at least one ligand, or more particularly of diethyldithiocarbamate-copper complex and at least one ligand, in the form of a molecular complex assembly typically involving multiple molecules of the dithiocarbamate-copper complex and multiple ligand molecules of one or several types. The particle preferably has the size in the range of 1-2000 nm. The particulate form is preferably substantially free of organic solvents.

According to the present invention, the complex particle is prepared by combining at least one ligand with a first component selected from a dithiocarbamate or a metal salt in an aqueous solvent, and simultaneously or subsequently adding a second component selected from a dithiocarbamate or a metal salt, whereas if the first component is a dithiocarbamate, then the second component is a metal salt; and if the first component is a metal salt, then the second component is a dithiocarbamate.

Within the framework of the present invention, it was discovered that when the simultaneous or sequential addition of the reagents is carried out as described herein, then after the addition of the second component, the ligand has a considerable capacity to bind to the dithiocarbamate-metal compound that is rapidly formed in the solution and spontaneously assemble into higher molecular complex assemblies, typically of the size within the range 1-2000 nm, thus forming a bioavailable dispersion. In this form the molecules of dithiocarbamate-copper complex are uniformly distributed within the assembly, maintain their original chemical properties and exhibit a substantially improved biological activity, both in vitro and in vivo, thus enabling the therapeutic or diagnostic use of an otherwise water-insoluble compound, including the use in cancer treatment and tumour imaging.

The process of complex particles preparation can be performed in a very short time (below 1 minute), in a single reaction vessel without the need for organic solvents and which allows either immediate or sustained parenteral, topical or per-oral administration.

The present invention further includes a kit of parts comprising a dithiocarbamate, a metal salt, at least one ligand, a sterile aqueous solvent wherein the aqueous solvent is preferably water or water-based buffer, and a container for combining the at least one ligand, the dithiocarbamate and the metal salt in the aqueous solvent under sterile conditions. The components of the kit may be provided in separate containers within the kit.

The particles of the present invention have a number of advantages. The non-human origin of the polymers and detergents removes ethical, safety and immunotoxicity issues which are connected with blood protein ligands. The particles are stable, do not undergo denaturation due to low or high pH values or in high temperatures, they are resistant to enzymes such as proteases. The ligands are commercially available on industrial scale and non-toxic. The possibility to use various polymers and/or detergents allows fine-tuning the final desired physico-chemical properties of the resulting particles.

DETAILED DESCRIPTION OF THE INVENTION

In the present invention, "molecular complex assembly particles" mean multinuclear molecular complex particles, wherein typically one particle contains one or several molecules of bis-dithiocarbamate metal complex and one or several molecules of the ligand. The molecular complex corresponds to a complex formed by at least two molecules which are typically bound together by non-covalent bonds.

The wording "particular form" means "particles".

In the present invention, "metal" means a metal selected from transition metals (or d-metals) and metals of the IIIA and IVA groups of the periodic table. Preferably, metals are transition metals. More preferably, the metal is selected from copper, zinc, cadmium, mercury. Most preferably, the metal is copper. All advantages of the present invention are most strongly pronounced for copper.

The metal may be in the form of a single isotope or an isotopic mixture. The isotopes may be radioactive isotopes or non-radioactive isotopes. For copper, non-radioactive isotopes are $^{63}$Cu and $^{65}$Cu, and radioactive isotopes are preferably $^{64}$Cu or $^{67}$Cu. $^{64}$Cu is a positron emitting isotope of copper, with applications for molecular radiotherapy and positron emission tomography.

"Metal salt" means a salt of the metal in the form of a cation with an anion. With regard to the intended pharmaceutical use of the particle dispersion (a dispersion of larger particles may also be referred to as a suspension), the skilled person would understand that the anion should be a pharmaceutically acceptable anion and preferably water-soluble. The anion may be selected, e.g. from inorganic acid anions such as halogenides (in particular chlorides, bromides, iodides), sulfates, sulfites, sulfides, phosphates, nitrates, carbonates; carboxylic acid anions, dicarboxylic acid anions, tricarboxylic acid anions, sulfonic acid anions, amino acid anions, such as formates, acetates, propionates, oxalates, succinates, maleinates, fumarates, maleates, citrates, triflates, gluconates, bis-glycinates.

"Dithiocarbamate" means a moiety having the formula (R1)(R2)N—CS$_2^-$ (also referred to in this text as R1,R2-dithiocarbamate), wherein R1 and R2 are the same or different and are independently selected from C1-C8 alkyl, C2-C8 alkenyl, C3-C10 cycloalkyl, C6-C14 aryl, C4-C14 heteroaryl containing at least one heteroatom selected from O, S, N, C3-C10 heterocyclyl containing at least one heteroatom selected from O, S, N; or R1 and R2 together with the nitrogen atom on which they are bound form a heterocycle, wherein —R1-R2- is a C2-C6 alkylene or a C2-C6 alkenylene, wherein optionally 1-2 carbon atoms may be replaced by heteroatoms selected from O, S, NH. The moieties forming R1 and R2 may be unsubstituted or further substituted by at least one substituent selected from C1-C4 alkyl, hydroxy, mercapto, C1-C4 alkoxy, C1-C4 alkylthio, halogen, phenyl, benzyl, keto group, carboxyl group, C1-C4 alkyloxycarbonyl.

More preferably, R1 and R2 are independently selected from C1-C6 (or C1-C4) alkyl, C2-C6 (or C2-C4) alkenyl, C3-C6 cycloalkyl, phenyl; or R1 and R2 together with the nitrogen atom on which they are bound form a heterocycle, wherein —R1-R2- is a C2-C6 alkylene or a C2-C6 alkenylene.

Most preferably, the dithiocarbamate is diethyldithiocarbamate (R1 and R2 are ethyl).

Dithiocarbamate can be present in the form of a negatively charged anion, typically in the dithiocarbamate-metal complex. As a starting compound in the process of the present invention, it may be used in the form of a neutral compound (R1)(R2)N—C(S)SH or, preferably, in the form of a salt [(R1)(R2)N—CS$_2$]$^{m-}$Cat$^{m+}$, such as alkali metal salt (Cat$^+$ is an alkali metal cation, m=1), ammonium salt (Cat$^+$ is an ammonium cation, m=1) or alkaline earth metal salt (Cat$^+$ is an alkaline earth metal cation, m=2). The skilled person understands which form is meant or which form is necessary, depending on the context in which the term "dithiocarbamate" is used.

"Dithiocarbamate-metal compound" comprises at least one dithiocarbamate moiety and at least one metal, preferably one metal. For example, the dithiocarbamate-metal compound may correspond to formula (I)

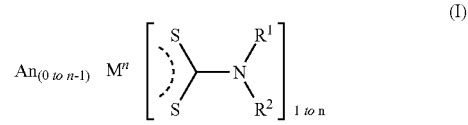

(I)

wherein
M is a metal, preferably copper,
An is a pharmaceutically acceptable anion, preferably as defined herein above,
n is the valence of the metal, typically, n is 1, 2, or 3,
and R1 and R2 are as defined herein above.

The ratio of the metal to dithiocarbamate may be for example in the range of from 1:5 to 5:1, or in the range of 1:2 to 5:1. The ratio of the metal to dithiocarbamate may optimally correspond to their stoichiometric ratio in the compound, or to their stoichiometric ratio±20%, or to their stoichiometric ratio±50%. For example, for copper the stoichiometric ratio is 1:2.

"Ligands" are substances which significantly enhance solubility and absorption of dithiocarbamate-metal complexes by forming the molecular complex assembly particle and allowing per-oral, topical and parenteral administration of the said particle in human and veterinary medicine.

Ligands are selected from water-soluble polymers and detergents.

The polymers are non-peptide polymers, i.e., polymers not containing L-amino acids as monomeric units. The polymers may have number-average molecular weight in the range of 1 kDa to 10 MDa. The polymers may include polysaccharides, polyoxyalkylenes, polyalkylene glycols, polyvinylpyrrolidones, polyvinyl alcohols, polyhydroxyacids, polyacrylates, polymethacrylates, polyacrylamides, polymethacrylamides, polyethylene glycol ethers, poly-D-amino acids, stearic acid based polymers, gelatine based polymers, nucleic acids, mixed copolymers. More particularly, the polymers include cellulose and cellulose derivatives, glycosaminoglycans and their derivatives, cyclodextrins and their derivatives, starch and starch derivatives, poloxamers (polyoxyethylene-polyoxypropylene block copolymers), macrogols (polyethylene glycols) and their derivatives, polyvinylpyrrolidone, polyvinyl alcohols, polylactic acid, polyacrylates, polymethacrylates, polyacrylamides, polymethacrylamides, polyethoxylated castor oil, stearic acid based polymers, gelatine based polymers, ribonucleic acid, deoxyribonucleic acid, polyvinyl caprolactam-polyvinyl acetate-polyethylene glycol graft co-polymer.

More specifically, the polymers include cellulose, methylcellulose, hydroxypropylmethylcellulose, Ficoll, starch, hydroxyethyl starch (Voluven®), hyaluronic acid, chondroitin sulphate, sulphobutylether-beta-cyclodextrin (Captisol®), poloxamers (e.g. Pluronic® F-127), macrogol, macrogolglycerol ricinoleate, macrogol 15 hydroxystearate, polyvinylpyrrolidone (PVP), polyvinyl alcohols (PVA), polylactic acid, poly(N-(2-hydroxypropyl)methacrylamide) (HPMA), polyethoxylated castor oil (e.g. cremophor), polyvinyl caprolactam-polyvinyl acetate-polyethylene glycol graft co-polymer (Soluplus® BASF), polyoxyethylated 12-hydroxystearic acid (Solutol® HS 15 (BASF)), succinylated gelatine (Gelaspan®), ribonucleic acid, deoxyribonucleic acid.

Even more specifically, the polymers are selected from Pluronic® F127 (poly(ethylene glycol)-block-poly(propylene glycol)-block-poly(ethylene glycol), polyvinylpyrroline (povidone), hydroxypropylmethylcellulose, polyvinyl caprolactam-polyvinyl acetate-polyethylene glycol graft co-polymer (Soluplus®), sulphobutylether-beta cyclodextrin (Captisol®).

Detergents are pharmaceutically acceptable water-soluble detergents, in particular steroid-based detergents, more particularly cholates and cholate derivatives such as cholate salts. The detergents are preferably sodium ursodeoxycholate or sodium deoxycholate.

"Aqueous solvent" is water or a water-based buffer, such as phosphate, citrate, acetate, Tris, HEPES, saline, glucose solution, or other common buffers. Preferably, the aqueous solvent is sterile.

The size of the self-assembled complex particles (i.e., molecular complex assemblies) is 1-2000 nm. Preferably, at least 90% of the complexes have the size within the range of 1-500 nm. In some embodiments, at least 50%, or at least 70%, or at least 90% of the particles have the size within the range of 1-1000 nm, or within the range of 10-500 nm, or within the range of 20-500 nm, or within the range of 1-220 nm. The complexes sizes and their distributions were measured by Dynamic Light Scattering (DLS) method and the term "size" or "average size" as used throughout this text refers to the average size as determined by DLS (Z-average).

The particulate form consisting of or comprising dithiocarbamate-metal complex and at least one ligand may be sterile filtered, preferably using a 0.22 micrometer filter.

The particulate form consisting of or comprising dithiocarbamate-metal complex and at least one ligand may be provided in the form of an injection or infusion liquid (solution, dispersion or suspension). The injection or infusion liquid further comprises at least one pharmaceutically acceptable excipient selected from buffers, surfactants, chelating agents, isotonicity adjustment agents, pH adjustment agents, preservatives, stabilisers, antioxidants, reducing agents, solubilizers, metal ions.

The particulate form consisting of or comprising dithiocarbamate-metal complex and at least one ligand may be provided in a dry form, in particular in a lyophilized (freeze-dried) form or in a spray-dried form. The lyophilized formulation typically further comprises at least one pharmaceutically acceptable excipients selected from cryoprotectants, buffers, surfactants, chelating agents, isotonicity adjustment agents, pH adjustment agents, preservatives, stabilisers, antioxidants, reducing agents, solubilizers, metal ions. The spray-dried formulation may further comprise at least one pharmaceutically acceptable excipients selected from buffers, surfactants, chelating agents, isotonicity adjustment agents, pH adjustment agents, preservatives, stabilisers, antioxidants, reducing agents, solubilizers, metal ions. In particular, lyophilization further improves stability, and thus facilitates storage and logistics.

The dry form may be further formulated as a powder for preparing liquid formulations, or in the forms suitable for peroral administration such as tablets, pills, soft capsules, hard capsules. The liquid or the dry form may be further formulated in forms suitable for topical administration such as lotions, ointments, creams, patches, dressings.

The buffers may include acetate, succinate, citrate, triethanolamine, arginine, phosphate buffers.

The surfactants may be, e.g., polysorbate 80, polysorbate 20, poloxamer 188, poloxamer 407.

The chelating agents may include sodium edetate, glutamic acid, aspartic acid.

The isotonicity adjustment agents may be selected, e.g., from mannitol, sodium or potassium chloride, sorbitol, dextrose.

The pH adjustment agents may be, e.g., acetic acid, hydrochloric acid.

The stabilizers may include arginine, methionine, glutamic acid, glycine, leucine, aspartic acid, fatty acids, phosphatidyl choline, ethanolamine, acetyltryptophanate, PEG, PVP (10, 24, 40), sorbitol, glucose, propylene glycol, ethylene glycol.

The antioxidants may include glycerin, ascorbic acid, cysteine HCl, thioglycerol, thioglycolic acid, thiosorbitol, glutathione, alpha-tocopherol, sodium disulfide.

The reducing agents are, e.g., thiols.

The solubilizer may be, e.g., alanine.

The metal ions may include $Ca^{2+}$, $Ni^{2+}$, $Mg^{2+}$, $Mn^{2+}$.

The preservatives may include phenol, benzyl alcohol, chlorobutanol, metacresol and parabens. Cryoprotectants (or lyoprotectants) may include monosaccharides, disaccharides, polysaccharides, amino acids, polysaccharides, polymers and other substances with cryoprotective properties, and derivatives thereof, in particular selected from mannitol, trehalose, saccharose, albumin, lactose, dextrose, sucrose, glucose, maltose, inositol, raffinose, inulin, maltodextrin, heparin, 2-hydroxypropyl-β-cyclodextrin, glycerol, sorbitol, mercaptans, polyethylene glycol, adonitol, amino acids, Tween 80, Pluronic, Brij, sodium dodecyl sulfate, ascorbic acid, polyvinylpyrrolidone (PVP K15), dextran.

The percentages, unless indicated otherwise, are w/w %.

The present invention describes the process of in-situ self-assembly of dithiocarbamate-copper compound and at least one ligand into a complex particle. This is attained by a process comprising the steps of:

(a) solubilizing at least one ligand in an aqueous solvent to a concentration in the range from 0.001% (w/w) to saturated solution (preferably from 0.1% to 10% (w/w))

(b) adding at least one dithiocarbamate dissolved in an aqueous solvent to a concentration in the range from 1 uM to 100 mM, preferably 1 to 10 mM;

(c) adding a metal salt solution in an aqueous solvent (e.g. water or water-based buffer), having the metal salt concentration in the range from 1 uM to 100 M, preferably 1 to 10 mM, wherein the steps are carried out in the sequence (a), (b), (c) or in the sequence (a), (c), (b), steps (b) and (c) can be performed simultaneously or subsequently.

Preferably, at least 10 second-delay accompanied by shaking or vortexing may be made between individual steps.

This single-tube reaction leads to rapid spontaneous self-assembly of ligand-dithiocarbamate-metal particles forming a dispersion.

In step (b), the dithiocarbamate is preferably in the form of a neutral compound or salt.

The ratio of the metal to dithiocarbamate may be for example in the range of from 1:5 to 5:1, or in the range of 1:2 to 1:5. The ratio of the metal to dithiocarbamate may optimally correspond to their stoichiometric ratio in the compound, or to their stoichiometric ratio±20%, or to their stoichiometric ratio±50%. For example, for copper the stoichiometric ratio of metal to dithiocarbamate is 1:2.

In a preferred embodiment, the molar ratio of metal ions:dithiocarbamate ions is 1:2.

The use of aqueous solvents yields the nanoparticulate form which is biologically compatible, without the need for further purification. If organic solvents would be used, which could be preferred for dissolving dithiocarbamate, the resulting particles would contain residual amounts of the organic solvents which are difficult to remove. This decreases the biocompatibility and bioavailability of the particles. Thus, within the framework of the present invention, it was surprisingly found that when the method of preparation is carried out in aqueous solvents, a water-soluble nanoparticulate form with a molecular assembly structure is formed, although dithiocarbamate has a low solubility in water. The use of aqueous solvents removes the disadvantages which would be due to the use of organic solvents.

The formed molecular complex particles of the present invention form a bioavailable dispersion, and can be administered to a patient in need of such treatment. The dispersion can be used in therapy, in particular cancer therapy, both chemotherapy and radiotherapy, such as therapy of solid tumors including melanoma, non-small cell lung cancer, small cell lung cancer, renal cancer, colorectal cancer, breast cancer, pancreatic cancer, gastric cancer, bladder cancer, ovarian cancer, uterine cancer, lymphoma, prostate cancer, myeloma, adenocarcinoma of the colon, nodal or hepatic metastases, brain tumours and brain metastases. The dispersion can also be used in diagnostics, such as tumour imaging, e.g., by positron emission tomography.

It is important to note that when the reaction is performed according to the present invention, the resulting dispersion of ligand-dithiocarbamate-copper particles allows direct parenteral, topical or per-oral applications to the treated subject (human or animal) without the need of additional chemical or physical processing such as extractions, separations, product cleaning, concentration enhancement etc.

The starting materials for preparation of the particles according to the present invention are commercially available in sufficient purity grade and non-expensive, and the preparation procedure is simple and economically advantageous. For example, polyvinylpyrrolidone (Povidone), diethyldithiocarbamate and $CuCl_2$ are commonly commercially available in pharmaceutical grades. Such procedure does not require costly chemical reactors, processing in additional devices and may simplify regulatory approval.

The reaction of the present invention can be performed directly at the bed of the patient or in the hospital pharmacy using a combination of pharmaceutically acceptable ingredients, such as the kit of parts as described above. This embodiment may significantly limit some of the logistic problems related to the storage of the dispersion—a fresh drug can be prepared when needed with high reproducibility and immediately applied.

The present invention also enables simple modification of the size of the assembled particles. By changing the ratio between dithiocarbamate-metal (in particular copper) complex and the ligands, the formed complex particles are of a different size. Optimum reaction conditions can be determined to produce complex particles with the optimum pharmacological properties, as the size of the particle is an important determinant of its behavior in-vivo, in particular for biodistribution (e.g. blood-brain barrier penetration) and kinetics.

The prepared dispersion of complex particles is stable and can be stored for several weeks at 4° C. without significant degradation or precipitation. The formed complex particles of ligand-dithiocarbamate-metal can be further stabilized by lyoprotectants which are mentioned above and processed by drying or lyophilisation to further improve stability, storage and logistics. Dried complex particles can be repeatedly dissolved in sterile water-based buffers and used for the therapy. This important aspect of the ligand-dithiocarbamate-metal complex particle properties is particularly valuable for both large- or small-scale industrial production, storage and logistics.

To prove general applicability of the complex particles, the following examples show preparation and characterization of dithiocarbamate-metal compound with selected pharmaceutically acceptable excipients or their combinations to demonstrate generic formulation and cancer targeting. The examples should not be construed as limiting the scope of the claimed invention.

BRIEF DESCRIPTION OF DRAWINGS

FIG. 1: table with average sizes of particles measured by the dynamic light scattering (DLS) prepared according to Examples 1-5. The particles form a polydispersed system which average size is dependent on the used excipient spanning the range approx. 40-1100 nm.

FIG. 4: table with anticancer activities of particles prepared according to Examples 2, 3, 5-13 measured as the cytotoxic effect on selected cancer cell lines cultured in-vitro under standard conditions.

FIG. 5: table with anticancer activities of particles prepared according to Examples 1-17 measured as the cytotoxic effect on selected cancer cell lines cultured as tumour spheroids.

EXAMPLES

Materials and Methods

Figure 2:
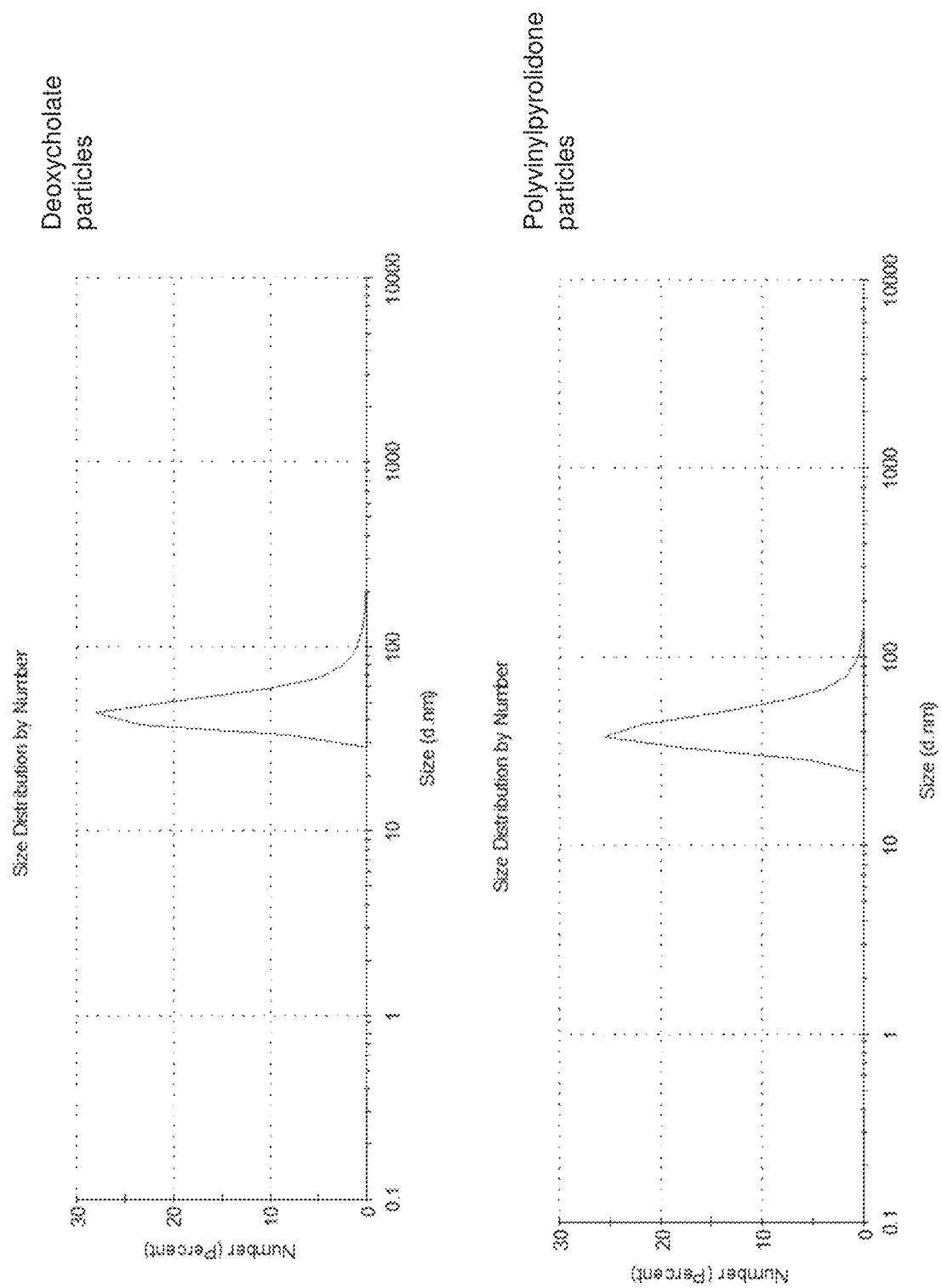
FIG. 2 shows representative dynamic light scattering (DLS) spectra of polydispersed system of particles prepared according to Example 1, 4, 5.

Dynamic Light Scattering (DLS) analyses allowing to determine the average size and size distribution of the prepared nanoparticles were performed by the Zetasizer Nano ZS instrument (Malvern, U.K.), with following parameters setting: V=400 uL, T=25° C., Number of runs: 10, Run duration: 1 s, Number of measurements: 3, Measurement angle: 173° Backscatter (NIBS default), Cell type: ZEN0040.

Cell Lines

Cell lines were cultured in appropriate medium supplemented with 10% fetal bovine serum and penicillin/streptomycin; and maintained at humidified, 5% CO2 atmosphere at 37° C. Cell lines were cultured in media as recommended by the suppliers and involved: U-2-OS (obtained from European Collection of Authenticated Cell Cultures, ECACC), CCRF-CEM (ATCC), K562 (ATCC), Cell line A549 (ATCC), K562 (ATCC), DLD-1 (ATCC), DU-145 (ATCC), HeLa (ATCC), BJ (ATCC), MRC5 (ATCC), HCT116 and its p53 gene knock-down counterpart (HCT116p53−/−), The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al 2002).

Cell Viability Test

MTS assays were carried out by robotic platform (HighResBiosolutions). Cell suspensions were prepared and diluted according to the particular cell type and the expected target cell density (25000-35000 cells/mL based on cell growth characteristics). Cells were added by automatic pipettor (30 μL) into 384 well microtiter plates. All tested formulations were prepared as described above, four folded dilutions of the intended test concentration were added in 0.15 μL aliquots at time zero to the microtiter plate wells by the echo acoustic non-contact liquid handler Echo550 (Labcyte). The experiments were performed in technical duplicates and three biological replicates at least. The cells were incubated with the tested compounds for 72 h at 37° C., in a 5% CO2 atmosphere at 100% humidity. At the end of the incubation period, the cells were assayed by using the MTS test. Aliquots (5 μL) of the MTS stock solution were pipetted into each well and incubated for additional 1-4 h. After this incubation period, the optical density (OD) was measured at 490 nm with an Envision reader (Perkin Elmer). Tumor cell survival (TCS) was calculated by using the following equation: TCS=(ODdrug-exposed well/mean ODcontrol wells)×100%. The IC50 value, the drug concentration that is lethal to 50% of the tumor cells, was calculated from the appropriate dose-response curves in Dotmatics software.

Tumour Spheroids Integrity Test

Spheroids were formed in CellCarrier clear-bottom 384WPs using a modified version of the liquid-overlay technique. For plate coating, a 0.75% (w/v) low-melting agarose (Sigma-Aldrich) stock solution was prepared in phenol red-free McCoy's medium without FBS. The agarose solution was then autoclaved to sterilize. Plates were coated with 15 μL of filtered 0.75% agarose by Multidrop Combi Reagent Dispenser (Thermo Fisher Scientific Oy, Vantaa, Finland) under sterile conditions. The coated plates were either used the same day or aseptically stored at 4° C. for up to 2 weeks. Cells were seeded at a density of $2.5 \times 10^4$ cells/mL per well in growth medium by Multidrop Reagent Dispenser using a Standard Tube Dispensing Cassette (Thermo Fisher Scientific Oy). The plates were then centrifuged at 4 g for 10 min and allowed to rest at RT for 1 h. The plates were left undisturbed for 4 days at 37° C. The medium was replaced regularly every 3 days by the EL406 washer manifold, and an equal volume of media was added by the peripump dispenser of the EL406. Spheroids were routinely monitored in an inverted Axio Observer.D1 fluorescence microscope (Carl Zeiss Microscopy GmbH, Jena, Germany).

High-Content Imaging and Image Analyses

HCT116, HeLa, DU145 and DLD1 spheroids were treated on day 6 by complex particles of dithiocarbamate copper compound with excipients or by copper diethyldithiocarbamate solution in DMSO for 72 h and imaged by a fully automated CellVoyager High-Content Imaging System (Model CV7000; Yokogawa Electric Corporation, Tokyo, Japan) using a 4× air objective. Bright-field z-stack images of spheroids were taken at an interval of 10-20 μm. Images were stored in the TIFF format, and spheroid characteristics were analyzed using an in-house algorithm developed in MatLab R2013b (MathWorks, Inc., Natick, MA). Briefly, the sharpest image with the maximum L1-norm of the image gradient was selected from the z-stack images. The visible well boundary was cropped from the image to prevent interference with subsequent image analysis. Next, the spheroid was localized by performing convolution with a predefined circular filter. Image segmentation was performed to correctly distinguish the spheroid (darker) from the lighter background. Once identified by the optimal threshold, spheroid characteristics, such as area and minor and major axis lengths, were computed in pixels.

Data were analyzed using GraphPad Prism (version 6; San Diego, CA).

HPLC/MS Analysis of Copper-Dithiocarbamate Complex (CuET)

The HR-MRM analysis was performed on HPLC-ESI-QTOF system consisting of HPLC chromatograph Thermo UltiMate 3000 with AB Sciex TripleTOF 5600+ mass spectrometer, using the DuoSpray ESI source operated at ion source voltage 5500 V, ion source gas flow rates 40 units, curtain gas flow rate 30 units, declustering potential 100 V and temperature 400° C. Data were acquired in Product ion mode with two parent masses 358.9 and 360.9 for analysis of CuET. Chromatographic separation was done by PTFE column especially designed for analysis of strong metal chelators filled by C18 sorbent. Analysis was performed at room temperature and flow rate 1500 μL/min with isocratic chromatography. Mobile phase consisted of HPLC grade acetone (Lachner) 99.9%, HPLC water (Merck Millipore) 0.1% and 0.03% HPLC formic acid (Sigma). Acquired mass spectra were evaluated in software PeakView 1.2, where extracted ion chromatograms of transitions 88.0 and 116.0 (common for both parent masses) with 0.1 mass tolerance was Gaussian smoothened with width of 2 points. Peak area was then recorded and recalculated to ng/ml according to calibration curve.

Sample Preparation for HPLC/MS Analysis

Liquid nitrogen-frozen biological samples were cut into small pieces by scalpel. Sample (30-100 mg) was immediately processed by homogenization in 100% acetone in ratio 1:10 sample vs. acetone (for plasma or serum the ratio was 1:4). Homogenization was done in a table homogenizer (Retsch MM301) placed in a cold room (4° C.) in 2 ml Eppendorf tube with 2 glass balls (5 mm) for 1 min, 30 Hz. Next, tube was immediately centrifuged at 4° C., 20.000 G, 2 min. Supernatant was decanted into a new 1.5 ml Eppendorf tube and immediately centrifuged for 30 min using small table centrifuge (BioSan FVL-2400N) placed inside a −80° C. freezer. Supernatant was quickly decanted into glass HPLC vial and kept at −80° C. not longer than 6 hours. Just before the HPLC analysis the vial was placed into the pre-cooled (4° C.) LC-sample rack and immediately analyzed. To enable approximate quantification of analyzed CuET, calibration curve was prepared. Standards were then processed similarly as the samples described above. Blood plasma samples were processed using similar procedure, just omitting the tissue homogenization step.

Mice In-Vivo Experiments

Acute toxicity study was done in NMRI mice animal model. Amount of complex particle of dithiocarbamate copper compound prepared according to example 1 and received by each animal was 1, 3 and 5 mg/kg intraperitoneally or intravenously. Maximum tolerated dose was defined as a concentration of the formulated drug which does not affect survival or induce morbidity in experimental animals.

Measurement of blood pharmacokinetics and tissue distribution was performed in mice injected with dithiocarbamate copper molecular assembly (at concentration corresponding to 1 mg/kg CuET).

Animals were sacrificed at indicated time points (typically 0.5, 1, 3, 6, 9, 12, 24 and 36 hours post injection), blood was collected and serum separated, selected organs were removed, snap frozen and stored together with serum at −80° C. until analysis.

Repeat-dose toxicity study was done in was done in NMRI mice animal model. Amount of complex particle of dithiocarbamate copper compound prepared according to example 1 and administered intraperitoneally at the dose of 1, 3 or 5 mg/kg of dithiocarbamate copper compound prepared according to example 1 was administered to each animal daily on days 1-5 and 8-12.

All aspects of the animal studies met the acceptance criteria for the care and experimental use of laboratory animals, and protocols were approved by the Animal Research Committee of Palacky University in Olomouc.

Chemicals Used:

Methylcellulose (Sigma-Aldrich), Hydroxypropylmethylcellulose (Sigma-Aldrich), Pluronic® F-127 (Sigma-Aldrich), polyvinylpyrrolidone (Kollidon®-17 (BASF), PVP40 (Sigma-Aldrich), PVP360 (Sigma-Aldrich)), polymethacrylamides (e.g. poly(N-(2-hydroxypropyl)methacrylamide) (HPMA)) (Sigma-Aldrich), cremophor (Sigma-Aldrich), Soluplus® (BASF), Gelofusine® 4% (Braun), poly-D-lysine (Sigma-Aldrich), Ficoll 400 (Sigma-Aldrich), Kolliphor® (BASF), Captisol® (Abmole), Solutol® HS 15 (BASF), hydroxyethyl starch (Voluven 10%, Fresenius Kabi), hyaluronic acid (Sigma-Aldrich), chondroitin sulphate (Sigma-Aldrich), deoxyribonucleic acid (salmon sperm DNA) (Sigma-Aldrich), sodium deoxycholate (Sigma-Aldrich).

Percentages, unless indicated otherwise, are w/w %.

Example 1

Preparation of Dispersion of Complex Particles from 2% Polyvinylpyrrolidone (PVP40, MW 40 kDa) and Diethyldithiocarbamate and Copper Chloride Salt.

Procedure:

Solution of 2% PVP40 in water is prepared. Diethyldithiocarbamate sodium salt (DTC) is solubilised in water in concentration 280 mM and added to 2% PVP40 to reach final concentration 5.6 mM, followed by brief stirring. To the 2% PVP40 solution containing 5.6 mM DTC is added sterile copper (ii) chloride (1 M concentration in water) to final concentration 2.8 mM, followed by brief stirring.

Results:

The resulting solution contains 2.8 mM (1 mg/ml) of diethyldithiocarbamate-copper-PVP40 complex particles. The complex particles resulting from this particular reaction were further analysed by DLS showing average size of 50+/−10 nm in diameter (see FIG. 1). The DLS spectra analyses also showed that the particles form a polydispersed system where the size of the particles spanned the range ca 20-100 nm with the largest fraction of 40-50 nm (see FIG. 2). The dispersion of particles was also tested in biological experiments involving cytotoxicity tests on cell grown in-vitro under standard cultivation conditions. The panel consisted of human cell lines derived from cancers including acute lymphoblastic leukemia (CCRF-CEM), lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (BJ, MRC5). Toxicity of the particles was tested in the MTS-based cell viability assay (see FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (see FIG. 5). Importantly, diethyldithiocarbamate-copper-PVP40 complex particles often display much better potency as neat diethyldithiocarbamate-copper powder dissolved in dimethyl sulfoxide (DMSO) (see FIG. 5).

The dispersion of complex particles was also tested in-vivo for acute and repeated dose toxicity intraperitoneally in mice showing MTD at doses corresponding to CuET concentration >3 and 1 mg/kg, respectively.

The dispersion of complex particles was also tested for the possibility of drying and subsequent re-solubilization. The nanoparticles were freeze-dried under vacuum for 16 hours. Dried powder was stored at 4° C. for one week and then solubilized with sterile water. Resulting re-solubilized particles were analysed by DLS displaying minimal changes in physical properties.

Example 2

Preparation of Dispersion of Complex Particles from 5% Polyvinylpyrrolidone (PVP40, MW 40 kDa) and Diethyldithiocarbamate and Copper Chloride Salt.

Procedure:

Solution of 5% PVP40 in water is prepared. Diethyldithiocarbamate sodium salt (DTC) is solubilised in water in concentration 280 mM and added to 5% PVP40 to reach final concentration 5.6 mM, followed by brief stirring. To the 5% PVP40 solution containing 5.6 mM DTC is added sterile copper (ii) chloride (1 M concentration in water) to final concentration 2.8 mM, followed by brief stirring.

Results:

The resulting solution contains 2.8 mM (1 mg/ml) of diethyldithiocarbamate-copper-PVP40 complex particles. The complex particles resulting from this particular reaction were further analysed by DLS showing average size of 50±10 nm in diameter (see FIG. 1). Size increase of diethyldithiocarbamate-copper-PVP40 complex particles was observed when 5% PVP solution was used for particle preparation. Such observation is proving that for instance, the original excipient concentration can affect the resulting size of particles. The DLS spectra analyses also showed that the particles form a polydispersed system where the size of the particles spanned the range ca 20-100 nm with the largest fraction of 40-50 nm (see FIG. 2). The dispersion of particles was also tested in biological experiments involving cytotoxicity tests on cell grown in-vitro under standard cultivation conditions. The panel consisted of human cell lines derived from cancers including acute lymphoblastic leukemia (CCRF-CEM), lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (BJ, MRC5). Toxicity of the particles was tested in the MTS-based cell viability assay (see FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (see FIG. 5). Importantly, diethyldithiocarbamate-copper-PVP40 complex particles often display much better potency as neat diethyldithiocarbamate-copper powder dissolved in dimethyl sulfoxide (DMSO) (see FIG. 5).

Figure 3:
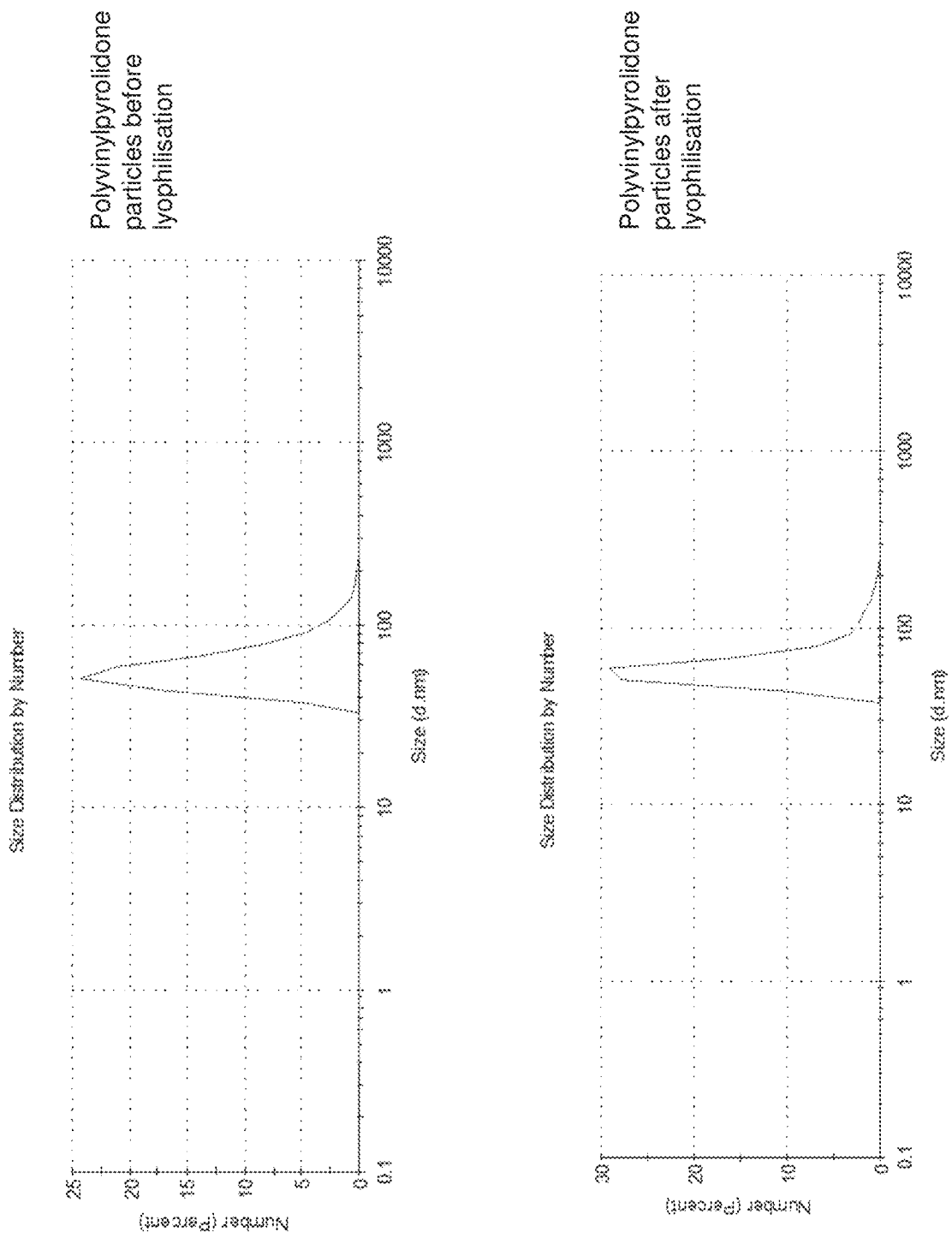
FIG. 3 shows representative dynamic light scattering (DLS) spectra of polydispersed system of particles prepared according to Example 2 depicting the minimum effect of lyophilisation on the particle size distribution.
Figure 6:
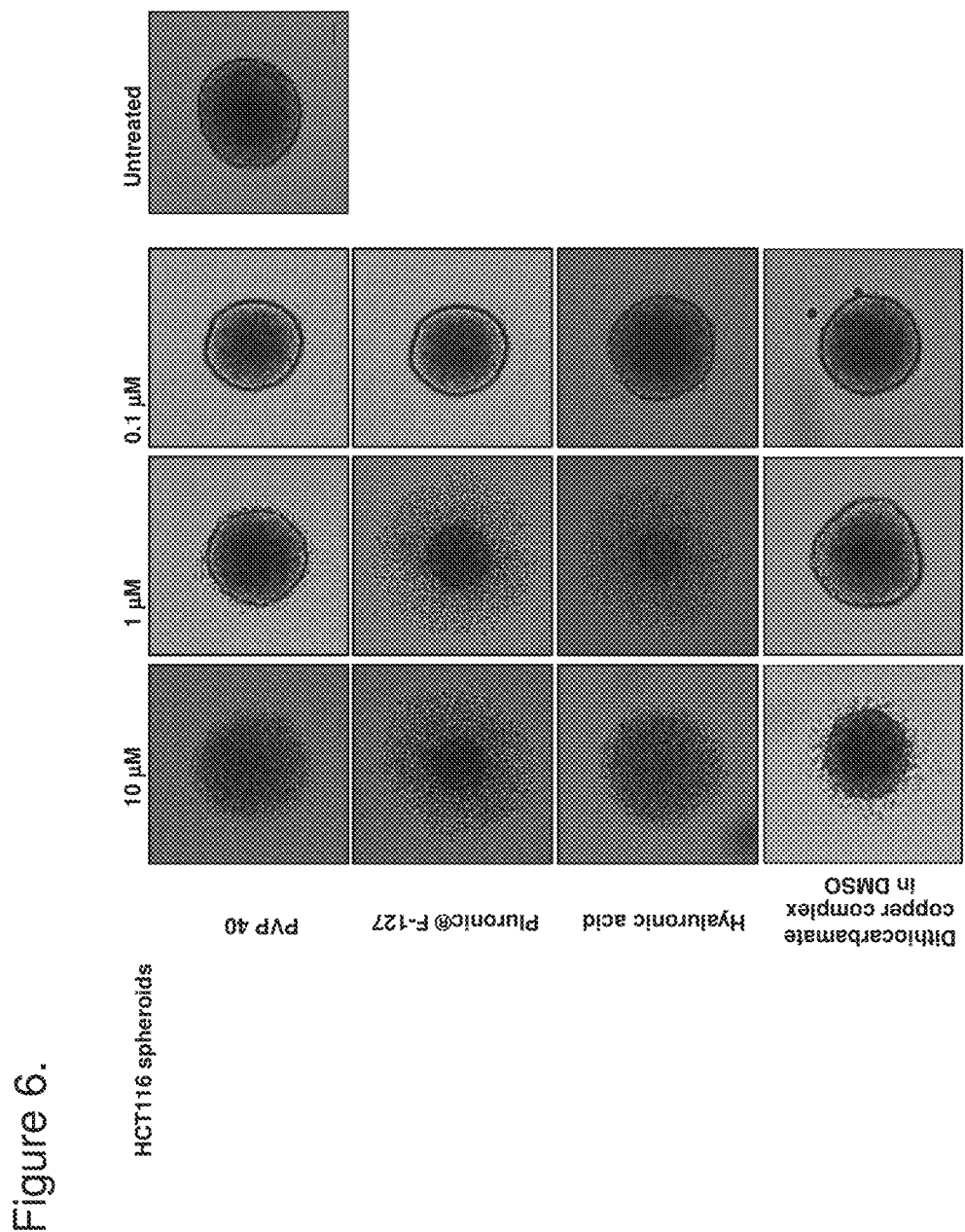
FIG. 6 depicts the effect of particles prepared according to Examples 2, 3 and 11 on the integrity of tumour spheroids. The figure shows images of 3D spheroids treated by particles of dithiocarbamate copper compound with various excipients.

The dispersion of complex particles was also tested for the possibility of drying and subsequent re-solubilization. The nanoparticles were freeze-dried under vacuum for 16 hours. The dried powder was stored at 4° C. for one week and then solubilized with sterile water. Resulting re-solubilized particles were analysed by DLS displaying minimal changes in the physical properties (FIG. 1—table 1, FIG. 3).

Example 3

Preparation of Dispersion of Complex Particles from 0.1% Hyaluronic Acid (HA) and Diethyldithiocarbamate and Copper Chloride Salt.

Procedure:

A solution of 0.1% hyaluronic acid (HA) in water is prepared. Diethyldithiocarbamate sodium salt (DTC) is solubilised in water in concentration 280 mM and added to 0.1% HA to reach final concentration 0.56 mM, followed by brief stirring. To the 0.1% HA solution containing 0.56 mM DTC is added sterile copper (ii) chloride (1 M concentration in water) to final concentration 0.28 mM, followed by brief stirring.

Results:

The resulting solution contains 0.28 mM (0.1 mg/ml) of diethyldithiocarbamate-copper-HA complex particles. The complex particles resulting from this particular reaction were further analysed by DLS showing average size of 1076+/−63 nm in diameter (FIG. 1). The dispersion of particles was also tested in biological experiments involving cytotoxicity tests on cell grown in-vitro under standard cultivation conditions. The panel consisted of human cell lines derived from cancers including lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (see FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (see FIG. 5). Importantly, diethyldithiocarbamate-copper-HA complex particles often display much better potency as neat diethyldithiocarbamate-copper powder dissolved in dimethyl sulfoxide (DMSO) (see FIG. 5).

Example 4

Preparation of Dispersion of Complex Particles from 0.75% Sodium Deoxycholate (DCH) and Diethyldithiocarbamate and Copper Chloride Salt.

Procedure:

Solution of 0.75% DCH in water is prepared. Diethyldithiocarbamate sodium salt (DTC) is solubilised in water in concentration 280 mM and added to 0.75% DCH to reach final concentration 5.6 mM, followed by brief stirring. To the 0.75% DCH solution containing 5.6 mM DTC is added sterile copper (ii) chloride (1 M concentration in water) to final concentration 2.8 mM, followed by brief stirring.

Results:

The resulting solution contains 2.8 mM (1 mg/ml) of diethyldithiocarbamate-copper-DCH complex particles. The complex particles resulting from this particular reaction were further analysed by DLS showing average size of 46.4+/−1.9 nm in diameter (FIG. 1). The DLS spectra analyses also showed that the particles form a polydispersed system where the size of the particles spanned the range ca 20-100 nm with the largest fraction of 40-50 nm (FIG. 2). The dispersion of particles was also tested in biological experiments involving cytotoxicity tests on cell grown in-vitro under standard cultivation conditions. The panel consisted of human cell lines derived from cancers including acute lymphoblastic leukemia (CCRF-CEM), lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (BJ, MRC5). Toxicity of the particles was tested in the MTS-based cell viability assay. The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-DCH complex particles often display much better potency as neat diethyldithiocarbamate-copper powder dissolved in dimethyl sulfoxide (DMSO) (FIG. 5).

The dispersion of complex particles was also tested in-vivo for acute and repeated dose toxicity intraperitoneally in mice showing MTD at doses corresponding to CuET concentration >5 and 1.5 mg/kg, respectively.

The dispersion of complex particles was also tested for the possibility of drying and subsequent re-solubilisation. The nanoparticles were freeze-dried under vacuum for 16 hours. Dried powder was stored at 4° C. for one week and then solubilized with sterile water. Resulting re-solubilized particles were analysed by DLS displaying minimal changes in the physical properties (FIG. 1, FIG. 3).

Example 5

Preparation of Dispersion of Complex Particles from 5% Soluplus® and Diethyldithiocarbamate and Copper Chloride Salt.
Procedure:
Solution of 5% Soluplus® in water is prepared. Diethyldithiocarbamate sodium salt (DTC) is solubilised in water in concentration 280 mM and added to 5% Soluplus® to reach final concentration 5.6 mM, followed by brief stirring. To the 5% Soluplus® solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-Soluplus® complex particles. The complex particles resulting from this particular reaction were further analysed by DLS showing average size of 53.4+/−2.7 nm in diameter (FIG. 1). The DLS spectra analyses also showed that the particles form a polydispersed system where the size of the particles spanned the range ca 20-100 nm with the largest fraction of 40-50 nm (see FIG. 2). The dispersion of particles was also tested in biological experiments involving cytotoxicity tests on cells grown in-vitro under standard cultivation conditions. The panel consisted of human cell lines derived from cancers including acute lymphoblastic leukemia (CCRF-CEM), lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (BJ, MRC5). Toxicity of the particles was tested in the MTS-based cell viability assay (see FIG. 4).

The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-Soluplus® complex particles often display much better potency as neat diethyldithiocarbamate-copper powder dissolved in dimethyl sulfoxide (DMSO) (FIG. 5).

The dispersion of complex particles was also tested for the possibility of drying and follow-up re-solubilisation. The nanoparticles were freeze-dried under vacuum for 16 hours. Dried powder was stored at 4° C. for one week and then solubilized with sterile water. Resulting re-solubilized particles were analysed by DLS displaying minimal changes in the physical properties.

Example 6

Preparation of Dispersion of Complex Particles from 0.2% Methylcellulose (MC) and Diethyldithiocarbamate and Copper Chloride Salt.
Procedure:
Solution of 0.2% MC in water is prepared. Diethyldithiocarbamate sodium salt (DTC) is solubilised in water in concentration 280 mM and added to 0.2% MC to reach final concentration 5.6 mM, followed by brief stirring. To the 0.2% MC solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-MC complex particles. The complex particles resulting from this particular reaction were further analysed by DLS showing average size of 233.6±98.13 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-MC complex particles often display much better potency as neat diethyldithiocarbamate-copper powder dissolved in dimethyl sulfoxide (DMSO) (FIG. 5).

Example 7

Preparation of Dispersion of Complex Particles from 5% Polyvinylpyrrolidone (PVP360, MW 360 kDa) and Diethyldithiocarbamate and Copper Chloride Salt.
Procedure:
Solution of 5% PVP360 in water is prepared. Diethyldithiocarbamate sodium salt (DTC) is solubilised in water in concentration 280 mM and added to 5% PVP360 to reach final concentration 5.6 mM, followed by brief stirring. To the 5% PVP360 solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-PVP360 complex particles. The complex particles resulting from this particular reaction were further analysed by DLS showing average size of 451.13±342.62 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-PVP360 complex particles often display much better potency as neat diethyldithiocarbamate-copper powder dissolved in dimethyl sulfoxide (DMSO) (FIG. 5).

Example 8

Preparation of Dispersion of Complex Particles from 5% Hydroxyethyl Starch (HES) and Diethyldithiocarbamate and Copper Chloride Salt.
Procedure:
A commercially available solution of 10% HES (Voluven®) is half diluted by H₂O to 5% HES which is used. Diethyldithiocarbamate sodium salt (DTC) is solubilised in water in concentration 280 mM and added to 5% HES to reach final concentration 5.6 mM, followed by brief stirring. To the 5% HES solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-HES complex particles. The complex particles resulting from this particular reaction were further analysed by DLS showing average size of 57.25±20.93 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-HES complex particles often display much better potency as neat diethyldithiocarbamate-copper powder dissolved in dimethyl sulfoxide (DMSO) (FIG. 5).

Example 9

Preparation of Dispersion of Complex Particles from 4% Succinylated Gelatine (SG) and Diethyldithiocarbamate and Copper Chloride Salt.
Procedure:
Commercially available solution of 4% SG (Gelofusine®) is used. Diethyldithiocarbamate sodium salt (DTC) is solubilised in water in concentration 280 mM and added to 5% HES to reach final concentration 5.6 mM, followed by brief stirring. To the 5% SG solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-SG complex particles. The complex particles resulting from this particular reaction were further analysed by DLS showing average size of 28.1±10.2 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-SG complex particles often display much better potency as neat diethyldithiocarbamate-copper powder dissolved in dimethyl sulfoxide (DMSO) (FIG. 5).

Example 10

Preparation of Dispersion of Complex Particles from 2% Chondroitin Sulfate (CHS) and Diethyldithiocarbamate and Copper Chloride Salt.
Procedure:
Solution of 2% CHS in water is prepared. Diethyldithiocarbamate sodium salt (DTC) is solubilised in water in concentration 280 mM and added to 2% CHS to reach final concentration 5.6 mM, followed by brief stirring. To the 2% CHS solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-CHS complex particles. The complex particles resulting from this particular reaction were further analysed by DLS showing average size of 298.17±32.07 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (see FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-CHS complex particles often display much better potency as neat diethyldithiocarbamate-copper powder dissolved in dimethyl sulfoxide (DMSO) (FIG. 5).

Example 11

Preparation of Dispersion of Complex Particles from 5% Pluronic® F-127 (PL) and Diethyldithiocarbamate and Copper Chloride Salt.
Procedure:
Solution of 5% PL in water is prepared. Diethyldithiocarbamate sodium salt (DTC) is solubilised in water in concentration 280 mM and added to 5% PL to reach final concentration 5.6 mM, followed by brief stirring. To the 5% PL solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-PL complex particles. The complex particles resulting from this particular reaction were further analysed by DLS showing average size of 74.54±9.5 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively. The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-PL complex particles often display much better potency as neat diethyldithiocarbamate-copper powder dissolved in dimethyl sulfoxide (DMSO) (FIG. 5). The dispersion of complex particles was also tested in-vivo for acute and repeated dose toxicity intraperitoneally in mice showing MTD at doses corresponding to CuET concentration >5 and >5 mg/kg, respectively. To measure circulating CuET concentrations, mice were dosed with single intraperitoneal or intravenous diethyldithiocarbamate-copper-PL complex particles (corresponding to 1 mg/kg of CuET) and sacrificed at 0.5, 1, 3, 6, 9, 12, 24, 36 hour time points. Serum was collected and frozen for analysis. Maximum measured concentration of CuET in serum was 15.92 nmol/l at 1 hour after intraperitoneal and 110.91 nmol/l at 0.5 hour after intravenous administration. Brain tissue was also collected and frozen for analysis. Maximum measured concentration of CuET in brain tissue was 2.21 nmol/l at 1 hour after intraperitoneal and 23.39 nmol/l at 0.5 hour after intravenous administration.

Example 12

Preparation of Dispersion of Complex Particles from 5% Cremophor (CR) and Diethyldithiocarbamate and Copper Chloride Salt.
Procedure:
Solution of 5% CR in water is prepared. Diethyldithiocarbamate sodium salt (DTC) is solubilised in water in concentration 280 mM and added to 5% CR to reach final concentration 5.6 mM, followed by brief stirring. To the 5% CR solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-CR complex particles. The complex particles resulting from this particular reaction were further analysed by DLS showing average size of 262.4±4.87 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (see FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-CR complex particles often display much better potency as neat diethyldithiocarbamate-copper powder dissolved in dimethyl sulfoxide (DMSO) (FIG. 5).

Example 13

Preparation of Dispersion of Complex Particles from 5% Solutol® HS 15 (SO) and Diethyldithiocarbamate and Copper Chloride Salt.
Procedure:
Solution of 5% SO in water is prepared. Diethyldithiocarbamate sodium salt (DTC) is solubilised in water in concentration 280 mM and added to 5% SO to reach final concentration 5.6 mM, followed by brief stirring. To the 5% SO solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-SO complex particles. The complex particles resulting from this particular reaction were further analysed by DLS showing average size of 45.08±23.32 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-SO complex particles often display much better potency as neat diethyldithiocarbamate-copper powder dissolved in dimethyl sulfoxide (DMSO) (FIG. 5).

Example 14

Preparation of Dispersion of Complex Particles from 0.2% Salmon Sperm DNA (DNA) and Diethyldithiocarbamate and Copper Chloride Salt.
Procedure:
Solution of 0.2% DNA in water is prepared. Diethyldithiocarbamate sodium salt (DTC) is solubilised in water in concentration 280 mM and added to 0.2% DNA to reach final concentration 5.6 mM, followed by brief stirring. To the 0.2% DNA solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-DNA complex particles. The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-DNA complex particles often display much better potency as neat diethyldithiocarbamate-copper powder dissolved in dimethyl sulfoxide (DMSO) (FIG. 5).

Example 15

Preparation of Dispersion of Complex Particles from 5% Kollidon® 17 (K17) and Diethyldithiocarbamate and Copper Chloride Salt.
Procedure:
Solution of 5% K17 in water is prepared. Diethyldithiocarbamate sodium salt (DTC) is solubilised in water in concentration 280 mM and added to 5% K17 to reach final concentration 5.6 mM, followed by brief stirring. To the 5% K17 solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-K17 complex particles. The complex particles resulting from this particular reaction were further analysed by DLS showing average size of 56.6±12.16 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively. The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-K17 complex particles often display much better potency as neat diethyldithiocarbamate-copper powder dissolved in dimethyl sulfoxide (DMSO) (FIG. 5).

The dispersion of complex particles was also tested in-vivo for acute and repeated dose toxicity intraperitoneally in mice showing MTD at doses corresponding to CuET concentration >5 and >5 mg/kg, respectively. To measure circulating CuET concentrations, mice were dosed with single intraperitoneal or intravenous diethyldithiocarbamate-copper-K17 complex particles (corresponding to 1 mg/kg of CuET) and sacrificed at 0.5, 1, 3, 6, 9, 12, 24, 36 hour time points. Serum was collected and frozen for analysis. Maximum measured concentration of CuET in serum was 38.23 nmol/l at 0.5 hour after intraperitoneal and 23.93 nmol/l at 0.5 hour after intravenous administration. Brain tissue was also collected and frozen for analysis. Maximum measured concentration of CuET in brain tissue was 16.38 nmol/l at 1 hour after intraperitoneal and 14.99 nmol/l at 0.5 hour after intravenous administration.

Example 16

Preparation of Dispersion of Complex Particles from 5% Ficol 400 (F400) and Diethyldithiocarbamate and Copper Chloride Salt.
Procedure:
Solution of 5% F400 in water is prepared. Diethyldithiocarbamate sodium salt (DTC) is solubilised in water in concentration 280 mM and added to 5% F400 to reach final concentration 5.6 mM, followed by brief stirring. To the 5% F400 solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-F400 complex particles. The complex particles resulting from this particular reaction were further analysed by DLS showing average size of 11.46±3.68 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (see FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-F400 complex particles often display much better potency as neat diethyldithiocarbamate-copper powder dissolved in dimethyl sulfoxide (DMSO) (FIG. 5).

Example 17

Preparation of Dispersion of Complex Particles from 5% Kolliphor EL (KEL) and Diethyldithiocarbamate and Copper Chloride Salt.
Procedure:
Solution of 5% KEL in water is prepared. Diethyldithiocarbamate sodium salt (DTC) is solubilised in water in concentration 280 mM and added to 5% KEL to reach final concentration 5.6 mM, followed by brief stirring. To the 5% KEL solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-KEL complex particles. The complex particles resulting from this particular reaction were further analysed by DLS showing average size of 158.67±24.31 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5). Importantly, diethyldithiocarbamate-copper-KEL complex particles often display much better potency as neat diethyldithiocarbamate-copper powder dissolved in dimethyl sulfoxide (DMSO) (FIG. 5).

Example 18

Preparation of Dispersion of Complex Particles from 5% Captisol® (Cap) and Diethyldithiocarbamate and Copper Chloride Salt.
Procedure:
Solution of 5% Cap in water is prepared. Diethyldithiocarbamate sodium salt (DTC) is solubilised in water in concentration 280 mM and added to 5% Cap to reach final concentration 5.6 mM, followed by brief stirring. To the 5% Cap solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-Cap complex particles. The complex particles resulting from this particular reaction were further analysed by DLS showing average size of 155.93±13.93 nm in diameter (FIG. 1). The dispersion of particles was tested in biological experiments involving cytotoxicity tests on cells grown in-vitro under standard cultivation conditions. The panel consisted of human cell lines as lung carcinoma (A549), colorectal adenocarcinoma (HCT116) and its p53 gene knock-down counterpart (HCT116p53−/−) is a model of human cancers with p53 mutation frequently associated with poor prognosis. The daunorubicin resistant subline of CCRF-CEM cells (CEM-DNR bulk) and paclitaxel-resistant subline K562-TAX were selected in our laboratory by the cultivation of maternal cell lines in increasing concentrations of daunorubicin or paclitaxel, respectively (Noskova et al. 2002). The osteosarcoma (U2OS), chronic myelogenous leukemia (K562) and primary (normal) cells including normal human fibroblasts (MRC5). Toxicity of the particles was tested in the MTS-based cell viability assay (FIG. 4). The dispersion of particles was also tested in biological experiments involving cytotoxicity tests on cancer cells spheroids mimicking tumour microenvironment and physiology. Tested tumour spheroid models included HCT116 (colorectal adenocarcinoma), DLD1 (colorectal adenocarcinoma), DU145 (metastatic prostate cancer) and HeLa (endocervical adenocarcinoma) cell lines (FIG. 5).

Importantly, diethyldithiocarbamate-copper-Cap complex particles often display much better potency as neat diethyldithiocarbamate-copper powder dissolved in dimethyl sulfoxide (DMSO) (FIG. 5).

The dispersion of complex particles was also tested in-vivo for acute and repeated dose toxicity intraperitoneally in mice showing MTD at doses corresponding to CuET concentration >5 and >5 mg/kg, respectively.

Example 19

Preparation of Dispersion of Complex Particles from 5% Poly(N-(2-Hydroxypropyl)Methacrylamide) (HPMA) and Diethyldithiocarbamate and Copper Chloride Salt.
Procedure:
Solution of 5% HPMA in water is prepared. Diethyldithiocarbamate sodium salt (DTC) is solubilised in water in concentration 280 mM and added to 5% HPMA to reach final concentration 5.6 mM, followed by brief stirring. To the 5% HPMA solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-HPMA complex particles. The complex particles resulting from this particular reaction were further analysed by DLS showing average size of 69.54±11.99 nm in diameter (FIG. 1).

Example 20

Preparation of Dispersion of Complex Particles from 1% Hydroxypropylmethylcellulose (HPMC) and Diethyldithiocarbamate and Copper Chloride Salt.
Procedure:
Solution of 1% HPMC in water is prepared. Diethyldithiocarbamate sodium salt (DTC) is solubilised in water in concentration 280 mM and added to 1% HPMC to reach final concentration 5.6 mM, followed by brief stirring. To the 1% HPMA solution containing 5.6 mM DTC is added sterile copper (ii) chloride (1 M concentration in water) to final concentration 2.8 mM, followed by brief stirring.
Results:
The resulting solution contains 2.8 mM (1 mg/ml) of diethyldithiocarbamate-copper-HPMC complex particles. The complex particles resulting from this particular reaction were further analysed by DLS showing average size of 330±23.16 nm in diameter (FIG. 1).

The dispersion of complex particles was also tested in-vivo for acute dose toxicity intraperitoneally and intravenously in mice showing MTD at doses corresponding to CuET concentration 3 and >5 mg/kg, respectively.

The invention claimed is:
1. A molecular complex assembly particulate form comprising dithiocarbamate-metal compound and at least one ligand, said particulate form being free of organic solvents,
  wherein the dithiocarbamate has a formula (R1)(R2)N—CH2S2—, wherein R1 and R2 are the same or different and are independently selected from C1-C8 alkyl, and
  wherein the ligands are water-soluble polymers selected from polyhydroxyacids, and stearic acid based polymers.

2. The particulate form according to claim 1, wherein the metal is selected from copper, zinc, silver and gold.

3. The particulate form according to claim 1, wherein the metal is selected from $^{63}$Cu, $^{65}$Cu, $^{64}$Cu and mixtures thereof.

4. A process for preparation of the molecular complex assembly particulate form according to claim 1, wherein the molecular complex assembly particular form is prepared by combining at least one ligand with a first component selected from a dithiocarbamate or a metal salt in an aqueous solvent, and simultaneously or subsequently adding a second component selected from a dithiocarbamate or a metal salt, whereas if the first component is a dithiocarbamate, then the second component is a metal salt; and if the first component is a metal salt, then the second component is a dithiocarbamate.

5. The process according to claim 4, comprising the steps of:
  (a) solubilizing at least one ligand in an aqueous solvent to a concentration in the range from 0.001% (w/w) to saturated solution;
  (b) adding at least one dithiocarbamate dissolved in an aqueous solvent in the range from 1 uM to 100 mM;
  (c) adding a metal salt solution in an aqueous solvent, having the metal salt concentration in the range from 1 uM to 100 M; and
  wherein the steps are carried out in the sequence (a), (b), (c) or in the sequence (a), (c), (b) or steps (b) and (c) are carried out simultaneously.

6. The process according to claim 4, wherein the molar ratio of metal ions: dithiocarbamate ions is 1:5 to 5:1.

7. The process according to claim 4, wherein the aqueous solvent is water or water-based buffer, such as phosphate, citrate, acetate, Tris, HEPES, saline, glucose solution.

8. The particulate form according to claim 1, wherein the particulate form is in a dry form, and further comprises at least one cryoprotectant selected from monosaccharides, disaccharides, amino acids, polysaccharides, and derivatives thereof, selected from mannitol, trehalose, saccharose, albumin, lactose, dextrose, sucrose, glucose, maltose, inositol, raffinose, inulin, maltodextrin, heparin, 2-hydroxypropyl-β-cyclodextrin, glycerol, sorbitol, mercaptans, polyethylene glycol, adonitol, amino acids, polyoxyethylene sorbitan fatty acid esters, polyoxyethylene-polyoxypropylene copolymer, polyoxyethylene alkyl ethers, sodium dodecyl sulfate, ascorbic acid, polyvinylpyrrolidone, dextran.

9. The particulate form according to claim 1, wherein the particulate form is in a lyophilized form and further comprises at least one cryoprotectant selected from monosaccharides, disaccharides, amino acids, polysaccharides, and derivatives thereof, selected from mannitol, trehalose, saccharose, albumin, lactose, dextrose, sucrose, glucose, maltose, inositol, raffinose, inulin, maltodextrin, heparin, 2-hydroxypropyl-β-cyclodextrin, glycerol, sorbitol, mercaptans, polyethylene glycol, adonitol, amino acids, polyoxyethylene sorbitan fatty acid esters, polyoxyethylene-polyoxypropylene copolymer, polyoxyethylene alkyl ethers, sodium dodecyl sulfate, ascorbic acid, polyvinylpyrrolidone, dextran.

10. The process according to claim 4, comprising the steps of:
  (a) solubilizing at least one ligand in an aqueous solvent to a concentration in the range from 0.001% (w/w) to saturated solution;
  (b) adding at least one dithiocarbamate dissolved in an aqueous solvent in the range from 1 to 10 mM;
  (c) adding a metal salt solution in an aqueous solvent, having the metal salt concentration in the range from 1 uM to 100 M; and
  wherein the steps are carried out in the sequence (a), (b), (c) or in the sequence (a), (c), (b) or steps (b) and (c) are carried out simultaneously.

11. The process according to claim 4, comprising the steps of:
  (a) solubilizing at least one ligand in an aqueous solvent to a concentration in the range from 0.001% (w/w) to saturated solution;
  (b) adding at least one dithiocarbamate dissolved in an aqueous solvent in the range from 1 uM to 100 mM;
  (c) adding a metal salt solution in an aqueous solvent, having the metal salt concentration in the range from 1 to 10 mM; and
  wherein the steps are carried out in the sequence (a), (b), (c) or in the sequence (a), (c), (b) or steps (b) and (c) are carried out simultaneously.

12. The process according to claim 4, comprising the steps of:
  (a) solubilizing at least one ligand in an aqueous solvent to a concentration in the range from 0.001% (w/w) to saturated solution;
  (b) adding at least one dithiocarbamate dissolved in an aqueous solvent in the range from 1 uM to 100 mM;
  (c) adding a metal salt solution in an aqueous solvent, having the metal salt concentration in the range from 1 uM to 100 M;
  wherein the steps are carried out in the sequence (a), (b), (c) or in the sequence (a), (c), (b) or steps (b) and (c) are carried out simultaneously; and
  (d) lyophilizing or drying the resulting solution.

13. The process according to claim 7, wherein the aqueous solvent is sterile.

* * * * *